(12) United States Patent
DeHeer et al.

(10) Patent No.: US 11,590,044 B2
(45) Date of Patent: Feb. 28, 2023

(54) DORSIFLEXION/PLANTARFLEXION EXTENSION ABOVE THE KNEE BRACE

(71) Applicant: IQ MEDICAL LLC, Carmel, IN (US)

(72) Inventors: Patrick DeHeer, Carmel, IN (US); John H. Moorin, Carmel, IN (US); Ricky Heath, Fishers, IN (US)

( * ) Notice: Subject to any disclaimer, the term of this patent is extended or adjusted under 35 U.S.C. 154(b) by 307 days.

(21) Appl. No.: 16/640,130

(22) PCT Filed: Jan. 12, 2018

(86) PCT No.: PCT/US2018/013430
§ 371 (c)(1),
(2) Date: Feb. 19, 2020

(87) PCT Pub. No.: WO2019/067008
PCT Pub. Date: Apr. 4, 2019

(65) Prior Publication Data
US 2020/0206059 A1     Jul. 2, 2020

Related U.S. Application Data

(60) Provisional application No. 62/563,629, filed on Sep. 26, 2017.

(51) Int. Cl.
*A61H 1/02*     (2006.01)
*A61F 5/01*     (2006.01)
*A61F 5/058*    (2006.01)

(52) U.S. Cl.
CPC ......... *A61H 1/0266* (2013.01); *A61F 5/0127* (2013.01); *A61F 5/0585* (2013.01); *A61F 2005/0158* (2013.01); *A61F 2005/0167* (2013.01); *A61H 2201/1253* (2013.01); *A61H 2201/165* (2013.01); *A61H 2201/1642* (2013.01)

(58) Field of Classification Search
CPC .......... A61H 1/0266; A61H 2201/1253; A61H 2201/1642; A61H 2201/165; A61H 2201/1673; A61H 1/02; A61F 5/0127; A61F 5/0585; A61F 2005/0158; A61F 2005/0167; A61F 5/042
See application file for complete search history.

(56) References Cited

U.S. PATENT DOCUMENTS

| 5,393 A | 12/1847 | Chamberlain |
| 73,768 A | 1/1868 | Allen |

(Continued)

FOREIGN PATENT DOCUMENTS

| DE | 102008052369 | 10/2008 |
| DE | 102008052517 | 7/2010 |

OTHER PUBLICATIONS

J.A. Radford, et al. "Does stretching increase ankle dorsiflexion range of motion? A systematic review." Br J Sports Med, Aug. 22, 2006, pp. 870-875, 40.

(Continued)

*Primary Examiner* — Tarla R Patel
(74) *Attorney, Agent, or Firm* — Gutwein Law; Greg N. Geiser

(57) ABSTRACT

Devices and processes used to treat ankle conditions. More specifically, the present disclosure relates to a brace and the corresponding method of use to treat ankle conditions by stretching the Gastrocnemius muscle, soleus muscle, and plantaris muscle.

12 Claims, 21 Drawing Sheets

(56) References Cited

U.S. PATENT DOCUMENTS

| | | | |
|---|---|---|---|
| 265,942 | A | 10/1882 | Burns |
| 2,516,872 | A | 8/1950 | Hauser et al. |
| 2,827,897 | A | 3/1958 | Pawlowski |
| 2,943,622 | A | 7/1960 | Nelson |
| 3,958,567 | A | 5/1976 | Callender, Jr. |
| 3,993,056 | A | 11/1976 | Rabischong et al. |
| 4,430,042 | A | 2/1984 | House |
| 4,632,096 | A | 12/1986 | Harris |
| 4,848,326 | A | 7/1989 | Lonardo |
| 4,872,448 | A | 10/1989 | Johnson, Jr. |
| 4,938,207 | A | 7/1990 | Vargo |
| 4,947,834 | A | 8/1990 | Kartheus et al. |
| 4,960,115 | A | 10/1990 | Ranciato |
| 4,981,132 | A | 1/1991 | Chong |
| 5,224,925 | A | 7/1993 | Varn |
| 5,378,223 | A | 1/1995 | Grim et al. |
| 5,462,517 | A | 10/1995 | Mann |
| 5,490,831 | A | 2/1996 | Myers et al. |
| 5,891,071 | A | 4/1999 | Stearns et al. |
| 5,891,077 | A | 4/1999 | Gilman et al. |
| 6,024,713 | A | 2/2000 | Barney |
| 6,048,326 | A | 4/2000 | Davis et al. |
| 6,096,942 | A | 8/2000 | Hack |
| 6,280,404 | B1 | 8/2001 | Morinaka et al. |
| 6,648,843 | B1 | 11/2003 | Marciano et al. |
| 7,077,818 | B2 | 7/2006 | Ingimundarson et al. |
| 7,462,159 | B1 | 12/2008 | Shlomovitz et al. |
| 7,922,677 | B2 | 4/2011 | Daiju |
| 7,950,909 | B2 | 5/2011 | Chang |
| 8,777,884 | B2 | 7/2014 | DeHeer et al. |
| 8,814,815 | B2 | 8/2014 | DeHeer et al. |
| 9,375,342 | B2 * | 6/2016 | DeHeer ................. A61F 5/0125 |
| 9,707,118 | B1 | 7/2017 | Meyer et al. |
| 2004/0030275 | A1 | 2/2004 | Morinaka |
| 2004/0002672 | A1 | 8/2004 | Carlson |
| 2009/0069732 | A1 | 3/2009 | Jackovitch |
| 2010/0069807 | A1 | 3/2010 | Cox |
| 2012/0283613 | A1 | 8/2012 | DeHeer et al. |
| 2012/0253253 | A1 | 10/2012 | DeHeer et al. |
| 2013/0247421 | A1 | 9/2013 | Santos |
| 2014/0114223 | A1 | 4/2014 | Ossur |
| 2021/0177636 | A1 * | 6/2021 | DeHeer .................... A61F 5/14 |

OTHER PUBLICATIONS

WIPO, Written Opinion of the International Searching Authority for PCT/US18/13430, 6 pages, dated Mar. 23, 2018.

WIPO, International Search report for PCT/US18/13430, 2 pages, dated Mar. 23, 2018.

Applicant, Revised Article 19 amendment for PCT/US18/13430, 1 page, dated Mar. 5, 2019.

Applicant, Replacement sheets for PCT/US18/13430, 5 pages, Mar. 5, 2019.

Applicant, Amended sheets for PCT/US18/13430, 5 pages, Mar. 5, 2019.

Applicant, Article 19 amendment for PCT/US18/13430, 1 page, dated Jan. 27, 2019.

WIPO, International Preliminary Report on Patentability for PCT/US18/13430, 7 pages, dated Mar. 31, 2020.

* cited by examiner

DORSIFLEXION/PLANTARFLEXION EXTENSION ABOVE THE KNEE BRACE

CROSS-REFERENCE TO RELATED APPLICATIONS

This application is a continuation application of International Patent Application No. PCT/US2018/13430, filed on Jan. 12, 2018, which claims the benefit of U.S. Provisional Application, Ser. No. 62/563,629, filed on Sep. 26, 2017, and incorporates the subject matter of each thereof in its entirety.

FIELD

The present disclosure relates to use of devices and processes to treat foot and ankle conditions. More specifically, the present disclosure relates to braces or device and their methods of use to treat ankle conditions by stretching the Gastrocnemius muscle, Plantaris muscle, or the Soleus muscles.

BACKGROUND OF THE INVENTION

Dorsiflexion is the movement of the foot toward the body by bending the ankle by drawing the toes backward toward the shins. Plantarflexion is the movement, of the foot away from the body by bending the ankle such as when standing on tiptoes or when pushing down on the gas pedal while driving. Both dorsiflexion and plantarflexion depend on the muscles of the ankle and calf to work properly.

Equinus is typically described as a condition in which the upward bending motion of the ankle is limited. Equinus is defined as the inability or lack of ankle joint dorsiflexion less than a right angle relative to the leg.

Equinus may result in a lack of flexibility past the right angle relative to the leg. Referring to FIGS. 1-3, someone suffering with equinus may lack the flexibility to bring the foot 18 past a right angle (90°) relative to the leg. A typical maximum ankle range of motion for dorsiflexion is indicated as twenty-five degrees (25°) less than a right angle relative to the leg. Equinus may also be characterized as a limited ankle range of motion for dorsiflexion which is no more than five (5°), ten (10°) or even fifteen degrees (15°) less than a right angle relative to the leg.

An injury to any one of the muscles supporting the act of plantarflexion will limit the range of motion of the foot. Ankle injuries are one of the most common ways to severely limit plantarflexion.

There are several possible causes for limited range of ankle motion. Limited range of ankle motion is often due to tightness in the calf muscles (the soleus muscle, the plantaris muscle and/or the gastrocnemius muscle). Shortening of the gastrocnemius muscle (also known as gastroc equinus) is a very common condition which may affect most people because the gastrocnemius muscle crosses two joints. Gastrocnemius muscle 24 originates above knee 12 joint, while soleus 26 originates below knee 12 joint. Both muscles join to form the Achilles tendon, which attaches to the heel. Therefore, the gastrocnemius muscle crosses two joints: knee 12 and ankle 16, while soleus muscle 26 only crosses ankle 16 joint.

Regardless of the cause of limited ankle motion, someone suffering with equinus can develop a wide range of foot problems. There are several ways to treat limited ankle range of motion, such as gastroc equinus, including stretching exercises, orthotics with heel lifts, padding, molded shoes, serial casting, as well as night splints, braces, and boots.

Many current night splints and braces are awkward and uncomfortable for sleeping. Since night splints and many current braces are supposed to be worn throughout the night, an awkward or cumbersome night splint or brace may cause user 22 to either not get a good night's sleep or cause user 22 to remove the device. If user 22 does not get a good night's sleep, user 22 may not choose to use the device in the future. This lack of compliance leads to the current devices not performing their intended function.

Both U.S. Pat. No. 8,777,884 (DeHeer, et al.) and U.S. Pat. No. 8,814,815 B2 (DeHeer, et al.), describe a hinged equinus brace device constructed with a footplate and a plurality of adjustable elongated rods (lateral and medial) to run along lateral and medial portions of the leg which extend above the knee of the user to the foot of the user for placement into the device.

U.S. Pat. No. 9,375,342 B2 (DeHeer et al.) describes a brace to treat ankle equinus. The brace locks the knee in full extension while clorsiflexing the ankle joint.

U.S. Pat. No. 7,922,677 (Daiju) describes a brace for rectification of clubfoot. The foot bottom plate can rotate 20 degrees in dorsiflexion and 45 degrees in, plaritarflexion. The brace includes a dorsal midfoot strap, and it does not include an ankle strap or toe wedge. There is no means to reduce painful friction to the heel, and the brace is not molded to gently approach the heel and Achilles tendon.

US Patent Application Pub No. 20040030275A1 (Morinaka) describes a body orthosis especially effective as a body corrective orthosis for talipes equinovarus. The foot sole plate can rotate 20 degrees in dorsiflexion and 45 degrees in plantarflexion. The brace includes a dorsal midfoot strap. However, there is no means to reduce painful friction to the heel, and the brace is not molded to gently approach the heel and Achilles tendon.

US Patent Application Pub No. 20130226059A1 (Philip George Littleavon Morris) describes an ankle foot orthopedic device for the treatment of various conditions of the ankle and foot. The device can be arranged to permit up to 90 degrees of plantarflexion and up to 30 degrees of dorsiflexion. The device does not contain a dorsal midfoot strap. However, there is no means to reduce painful friction to the heel, and the brace is not molded to gently approach the heel and Achilles tendon.

U.S. Pat. No. 9,707,118 B1 (Meyer at al.) describes a orthosis designed for increasing the range of motion and correcting the alignment of a patient's foot and ankle. The orthosis includes a dorsal midfoot strap but does not include an ankle strap. There are no means for plantarflexion. Dorsiflexion is limited to the range of approximately 18 to 22 degrees. There is no means to reduce painful friction to the heel, and the brace is not molded to gently approach the heel and Achilles tendon.

Therefore, a need remains for a device with ankle hinge positions which allow for either dorsiflexing or plantarflexing the ankle joint while extending the knee, where the device is molded to gently approach the heel and Achilles tendon.

A need also remains for a device that locks the knee in full extension while either dorsiflexing or plantarflexing the ankle joint.

SUMMARY OF THE INVENTION

The device of the present disclosure has more degrees in dorsiflexion than other devices while also holding the knee at full extension. The device can also hold the knee at full extension while also flexing the ankle.

The present disclosure includes a device for treating ankle equinus by stretching the Gastrocnemius muscle, the Plantaris muscle and soleus muscle. The present disclosure also includes a device for treating numerous foot and ankle deformities such as Achilles tendonitisitendonosis, plantar fasciitis, flatfoot, arch pain, forefoot pain, metatarsalagia, Morton's neuromas, diabetic forefoot ulcers, and others, such as conditions resulting from Myelomeningocele (Spina Bifida), Flexor Hallucis Longus Tendinosis, Anterior Ankle Impingement, and Plantar fasciitis.

In one embodiment of the invention, the brace further comprises a boot pad for the top of a user's foot while placed in the brace.

In another embodiment of the invention, the device may further comprise a wedge. The wedge may be located beneath the hallux of the user and may be configured to engage the user's Windlass Mechanism.

The present disclosure also includes a method of treating equinus by stretching the Gastrocnemius, soleus and plantaris muscles, the method comprising the steps of extending the knee of the user and dorsiflexing the foot by using a brace.

The present disclosure also include a method, of treating and plantar fasciitis by stretching the cmstrocnemius, soleus muscles and plantaris muscles, the method comprising the steps of extending the knee of the user and plantarflexing the foot by using a brace.

In one embodiment of the method, the method further comprises the step of measuring the angle of the ankle of the user using the brace.

From the present disclosure, the equinus is associated with any condition selected from the group consisting of Heel Spur Syndrome, Plantar fasciitis (also known as plantar heel pain), neuromuscular disorders including disorders selected from the group consisting of Cerebral Palsy and Friedreich's Ataxia, Congenital disorders including disorders selected from the group consisting of Congenital equinus, Clubfoot, Vertical Talus and Calcaneal Valgus, Pediatric Flexible Flatfoot deformity, Adult Flexible Flatfoot deformity, Tibialis Posterior Tendon Dysfunction or adult flat foot deformity, muscle strains, stress fractures, shin splints/Medial tibial stress syndrome, Iliotibial band syndrome, patellofemoral syndrome, ankle sprains or fractures, metatarsal or forefoot pain, metatarsophalangeal joint (MPJ) synovitis, hallux abducto valgus, hammer toes or claw toes, Lis franc's or Midfoot arthrosis, hallux limitus or hallux rigidus, forefoot calluses, Morton's neuroma, Chronic ankle instability, poor balance or increased fall rate in elderly, Sever's disease, lateral foot pain, Genu recurvatum, lower back pain, arch pain, ankle arthrosis, subtalar arthrosis, sesamoiditis, anterior compartment syndrome, forefoot nerve entrapment, Achilles tendonitis and tendonosis, Achilles tendon injuries, Haglund's Deformity, Retrocalcaneal heel spurs and tendonosis, Tarsal Coalitions, Bunion deformities, Metatarsalgia. Forefoot pain, Charcot deformity, Diabetic forefoot ulcers and toe ulcers, Equinovaros deformities from post-injury or post-stroke patients, Post Transmetatarsal or Chopart's amputation patients, Midfoot degenerative joint disease at Lis Franc's joint or Chopart's joint, Hypermobile first ray disorders and Cross-over toe deformities.

DETAILED DESCRIPTION OF THE INVENTION

For promoting an understanding of the principles of the invention, reference will now be made to certain embodiments illustrated in the disclosure, and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
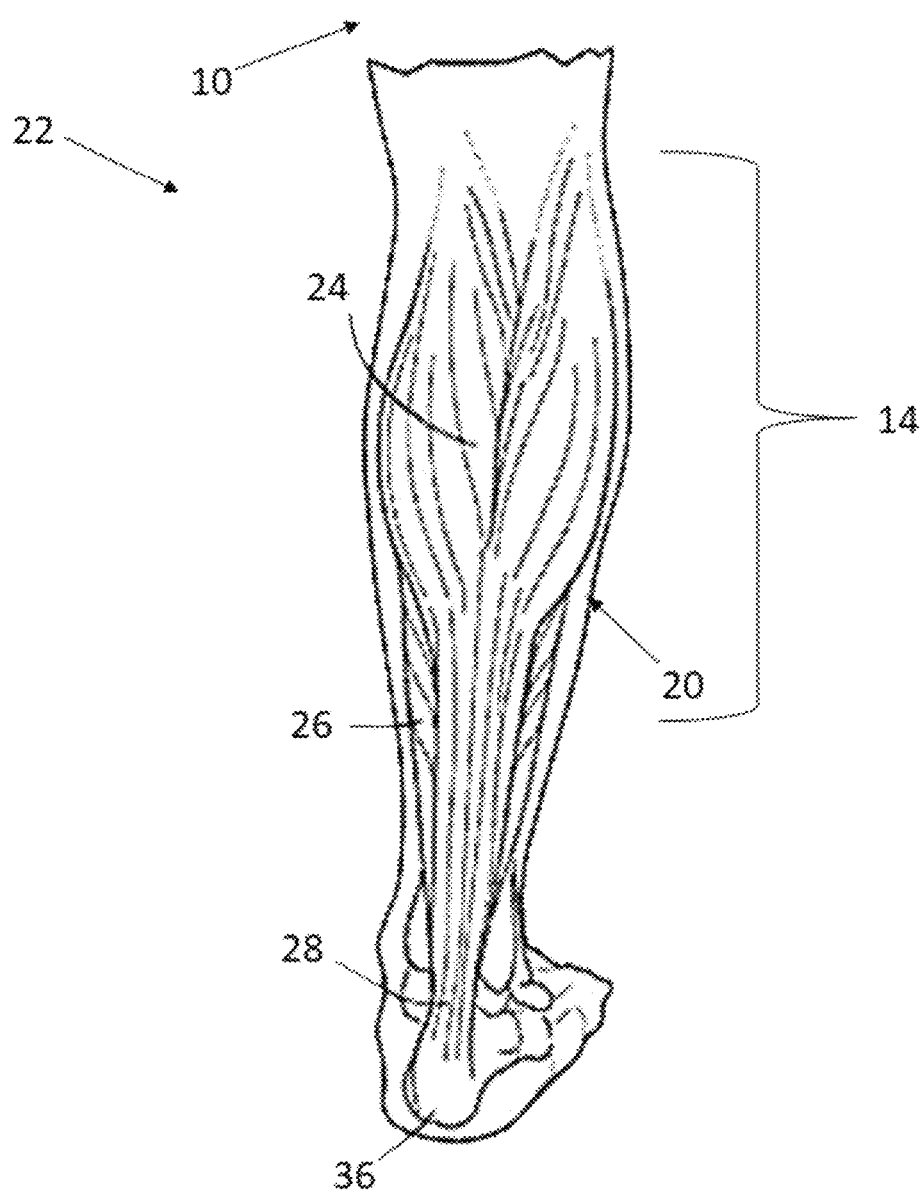
FIG. 1 is a back view of calf muscles with a knee at extension and an ankle at neutral position.
Figure 2:
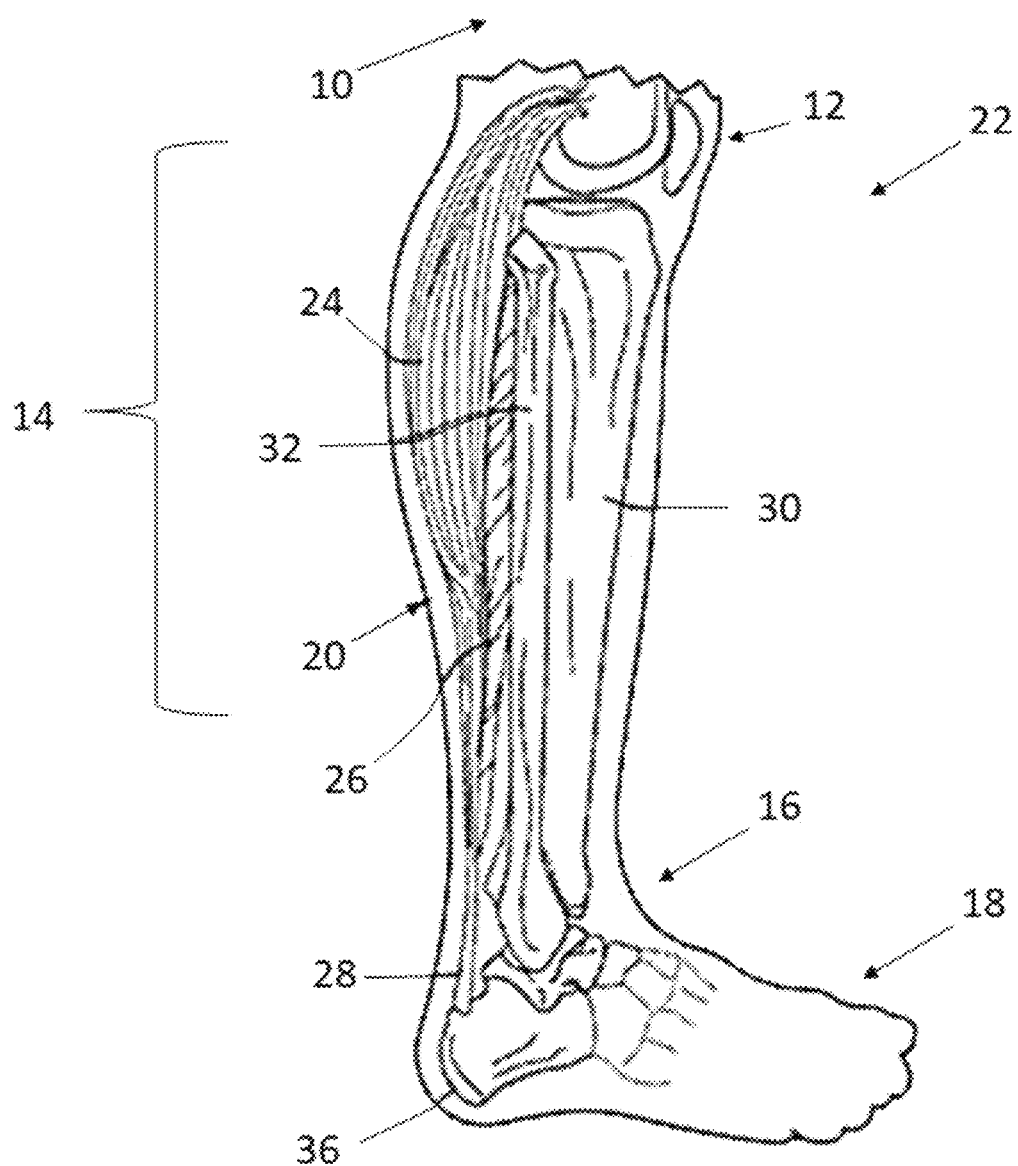
FIG. 2 is a side view of the calf muscles of FIG. 1.

As shown in FIGS. 1 and 2, thigh 10, knee 12, calf 14, ankle 16, foot 18, and calf muscles 20 of user 22 are illustrated. Calf muscles 20 are shown as gastrocnemius muscle 24 and soleus muscle 26. Each of these muscles 24, 26 shares a common insertion (attachment) via Achilles tendon 28 into the posterior calcaneus. Soleus muscle 26 originates at the proximal to posterior portions of tibia 30 and fibula 32. Soleus muscle 26 and gastrocnemius muscle 24 unite via their respective apponeurosis to form Achilles tendon 28. Unlike soleus muscle 26, gastrocnemius muscle 24 originates at posterior femur 34 just above knee 12 and also inserts into heel 36. Gastrocnemius muscle 24 crosses two joints: knee 12 and ankle 16.

As illustrated with knee 12 in extension and ankle 16 in normal position, soleus muscle 26 and gastrocnemius muscle 24 are not stretched to capacity in a person with normal ankle range of motion including maximum ankle dorsiflexion of twenty-five degrees (25'). In a person with limited ankle range of motion, such as equinus, soleus muscle 26 or aastrocnemius muscle 24 may be stretched to capacity with knee 12 in extension for gastroc equinus or gastrosoleal equinus and ankle 16 in normal position or in a dorsi flexed position.

Figure 3:
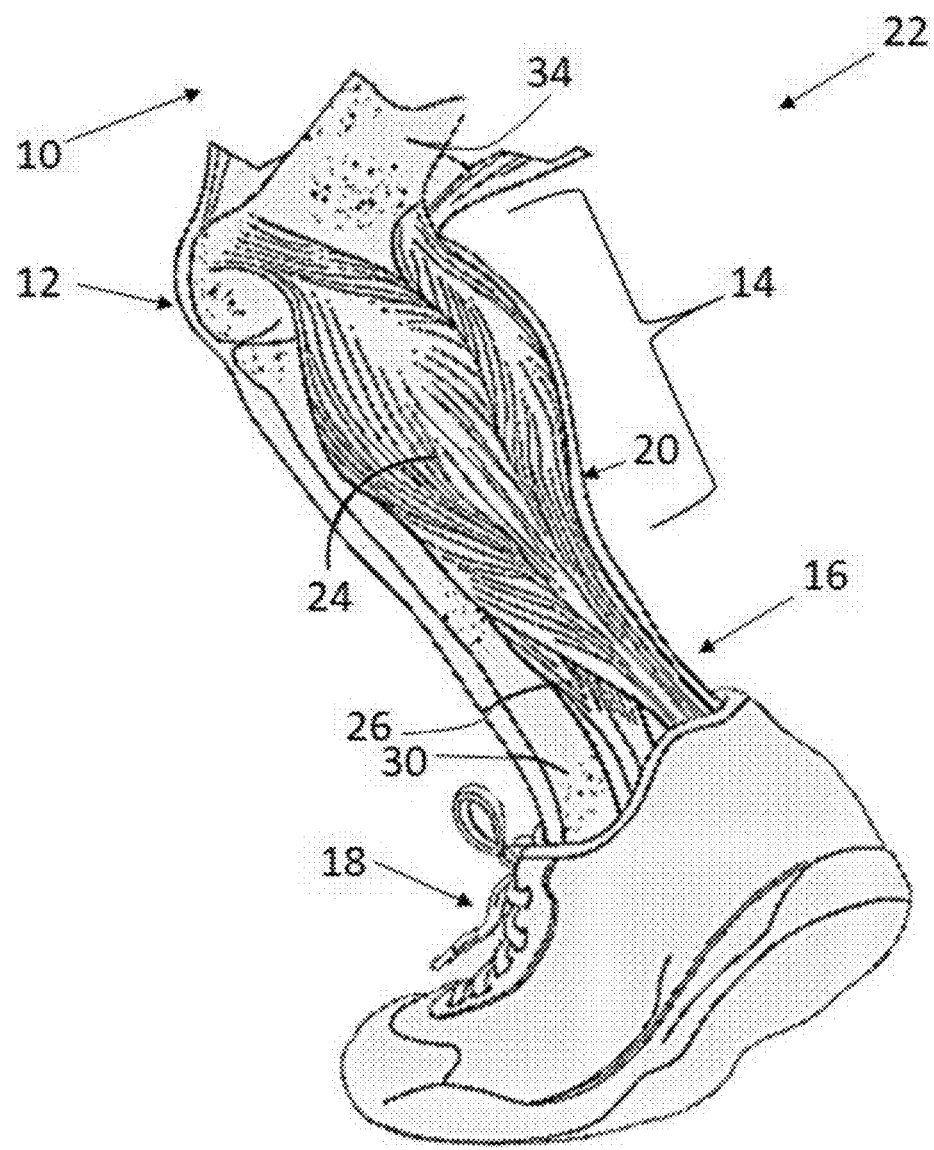
FIG. 3 is a perspective view of calf muscles with a knee in flexion and the ankle in dorsiflexion.

As illustrated in FIG. 3, a person with limited ankle range of motion due to gastroc equinus, moving knee 12 from extension to flexion releases gastrocnemius muscle 24 from full stretch capacity. A person suffering from gastroc equinus may be able to place ankle 16 in dorsiflexion with knee 12 in flexion even though gastrocnemius muscle 24 is shortened.

Figure 4:
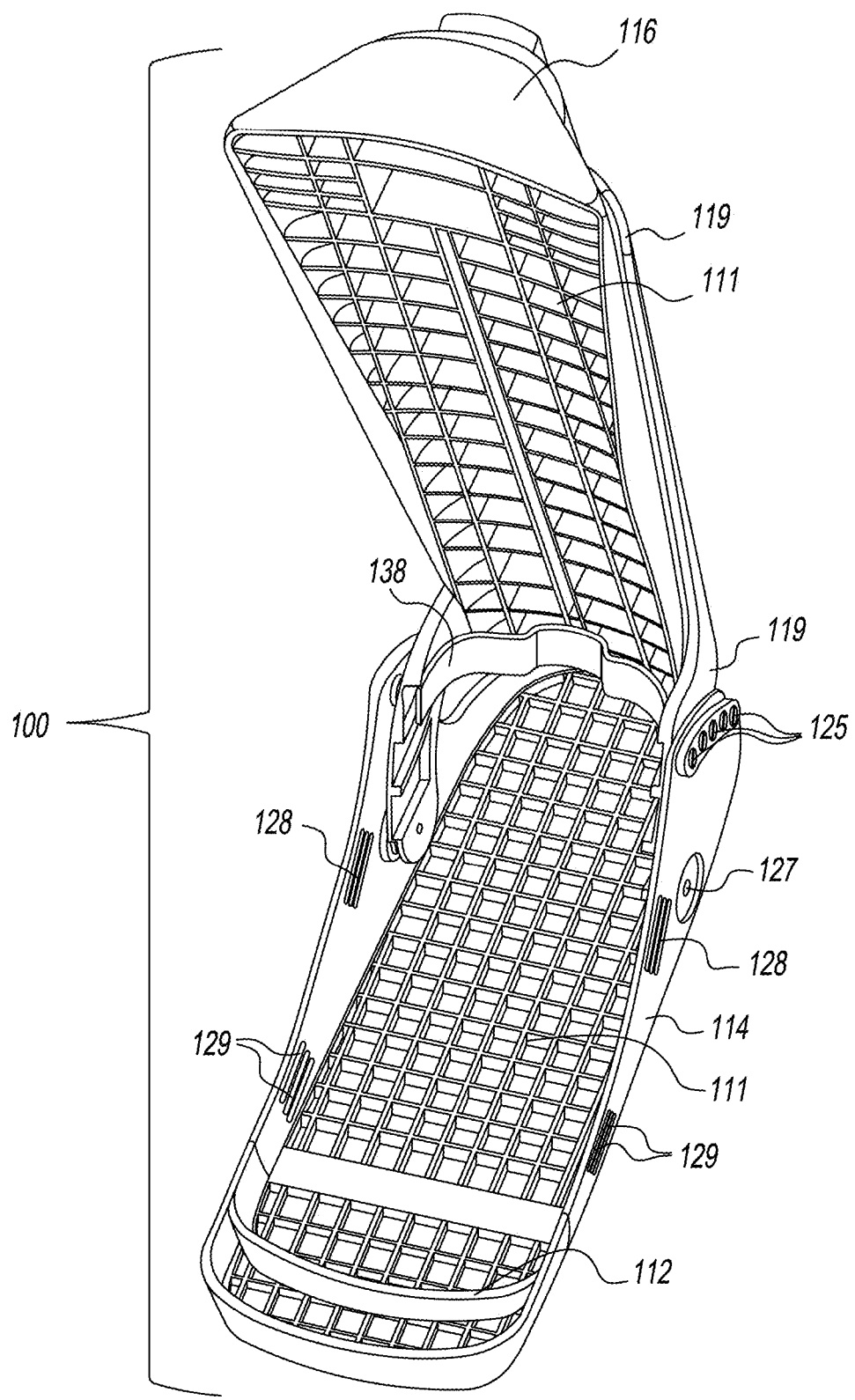
FIG. 4 is an illustration of the brace with a grid support structure and toe support.

As illustrated in one embodiment in FIG. 4, brace 100 may include a grid support structure 111 and toe support 112. Brace 100 is shown in a fully contracted form, slider 116 is in front of receiver 119. Support 138 bridges the two interior faces of receiver 119.

Figure 5:
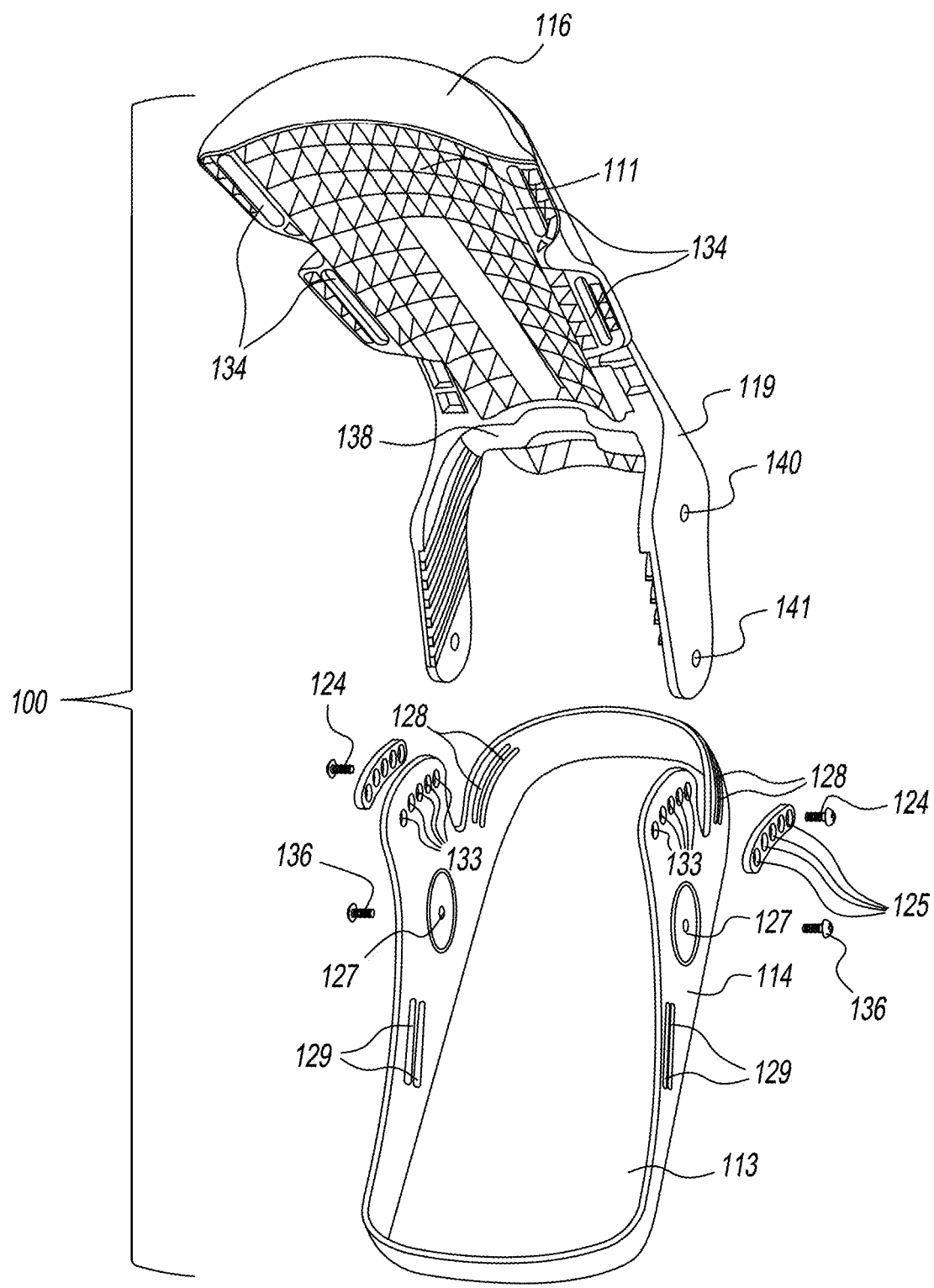
FIG. 5 is an exploded view of the brace with a foot plate.

An exploded view of the connection between boot 114 and receiver 119 in contracted brace 100 is illustrated in FIG. 5. Boot 114 may include foot plate 113 either with or without the grid support structure and toe support. Slider 116 includes openings 134 to secure leg straps 109 (see also FIG. 8). Support 138 is an integrated part of receiver 119 in this embodiment. Both sides of boot 114 are secured to receiver 119 by insertion of screw 136 into openina 127 and opening 141 on either side of both boot 114 and receiver 119 respectively.

The flexion angle of contracted brace 100 is controlled by insertion of screw 124 into one of the openings 125 and into opening 140 of receiver 119.

Figure 6:
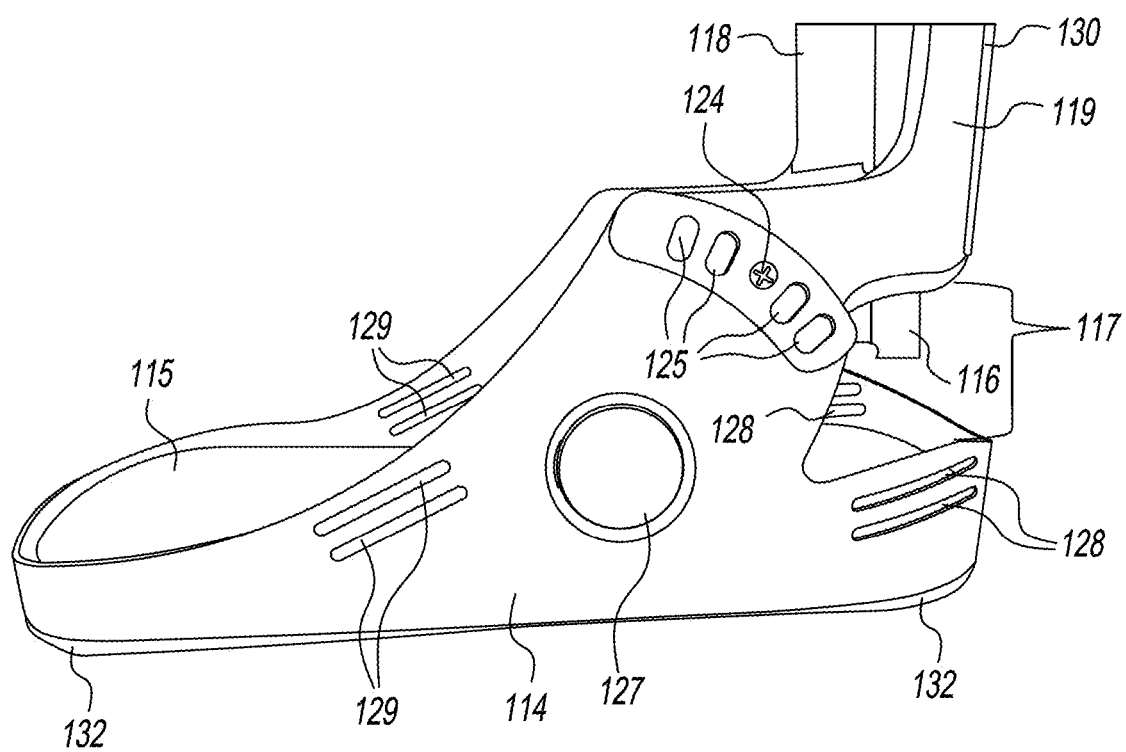
FIG. 6 is a side view of the boot in one embodiment of the brace, including boot pad and a fully contracted brace.

FIG. 6 is an illustration of a close up of the boot 114 of a fully contracted brace 100. Achilles opening 117 is between receiver 119 and boot 114. When the brace 100 is fully contracted, a bottom portion of slider 116 is visible beneath the top of the Achilles opening 117. Each side of boot 114 includes panel 127 to cover bolt 136 (as shown in FIG. 5).

Additional means for securing boot 114 to receiver 119 are also envisioned, such as a ball and socket multiplanar hinge.

Sole 132 is attached to the bottom of boot 114.

Boot 114 may include a boot pad 115.

Boot 114 includes a flexion angle region 139 which defines a plurality of flexion angle apertures 125. Screw 124 is configured to be located in any one of flexion angle apertures 125 and affixed to receiver 119. Placement of screw 124 in each flexion angle aperture 125 changes the flexion angle of foot 18 of user 22. Five flexion angle settings 125 are shown in this embodiment. Other divisions of flexion angle settings are envisioned down to an angle change of 5 or 10 degrees such as −20°, −10°, 0°, +10°, and +20°. Flexion angle settings 125 permit a flexion angle range of 40 degrees. Additional embodiments include a flexion angle range of up to 20 degrees.

Alternatively, flexion angle aperture 125 may comprise one or more slots in flexion angle region. For example, one continuous slot along each of the plurality of flexion angle apertures would facilitate placement of user's foot in any degree of plantarflexion or dorsiflexion orientation.

Additional alternative embodiments include a gear mechanism.

Additional means for affixing the flexion angle are also envisioned such as a snap lock mechanism of the peg-in-hole and the screw secure the ankle angle.

Boot 114 includes heel openings 128 to secure ankle strap 101.

Boot 114 includes tarsal openings 129. Tarsal openings 129 may be used to secure a boot lining 120.

Figure 7:
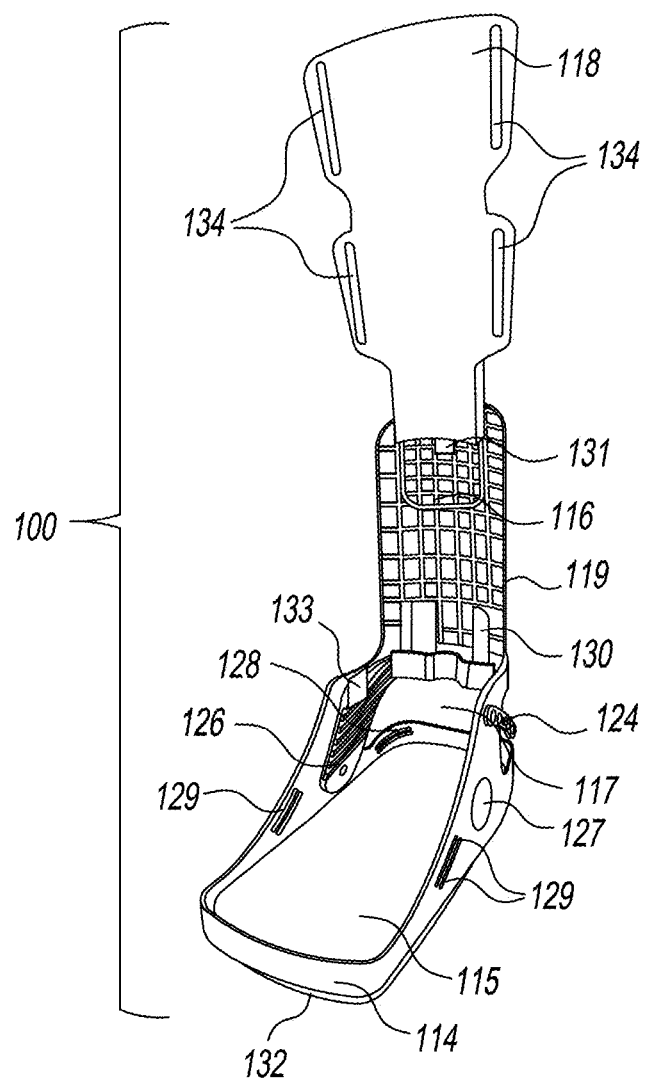
FIG. 7 is a front angled view of one embodiment of the fully extended brace, including boot pad and leg pad.

A fully extended brace 100 is illustrated in FIG. 7, including boot pad 115 and leg pad 118. The bottom of slider 116 is visible near the top of receiver 119. Achilles opening 117 is beneath receiver 119. Receiver 119 secures to boot 114 via bolts 126 and bolts 124. The outside of boot 114 includes panels 127 that cover bolts 126. The back of panel 130 is visible in openings in the bottom of receiver 119. The back of clip 131 is visible in openings that pass through both receiver 119 and slider 116.

Leg pad 118 and slider 116 both have openings 134 on both vertical sides for securing leg straps 109.

Figure 8:
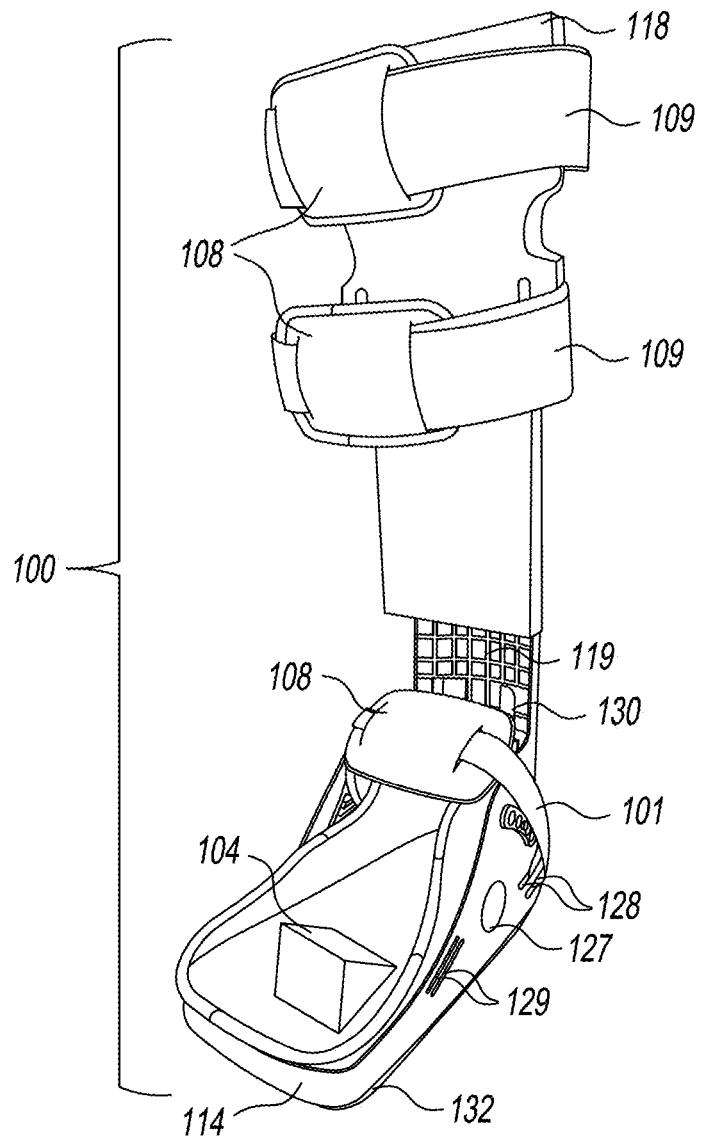
FIG. 8 is a front angled view of one embodiment of the fully extended brace, including boot pad (not shown), leg pad, leg straps, ankle strap, toe wedge, and boot lining. In this embodiment, the ankle strap is secured to the boot.

FIG. 8 illustrates a front angled view of the fully extended brace 100, including leg pad 118, leg straps 109, ankle strap 101, toe wedge 104, and boot lining 120.

Boot lining 120 may include openings for ankle strap 101.

Figure 9:
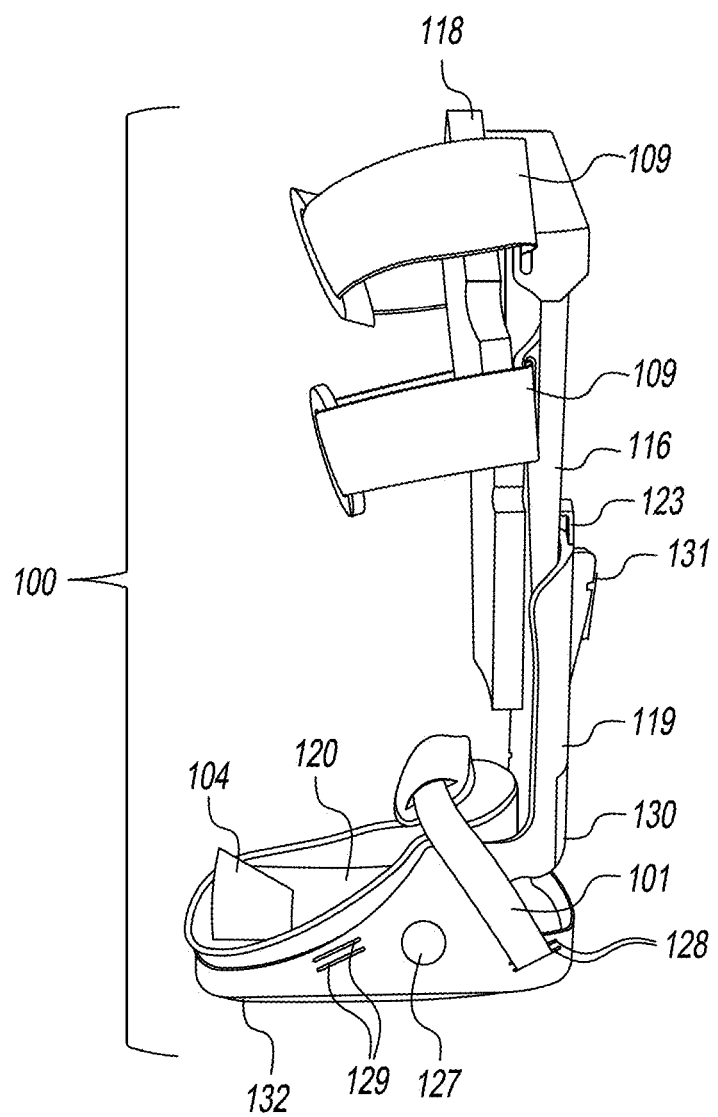
FIG. 9 is a side view of one embodiment of the fully extended brace of FIG. 8.

FIG. 9 illustrates a side view of the fully extended brace 100, including leg pad 118, leg straps 109, ankle strap 101, toe wedge 104, and boot lining 120. Ankle strap 101 is secured to boot 114 via heel openings 128.

Figure 10:
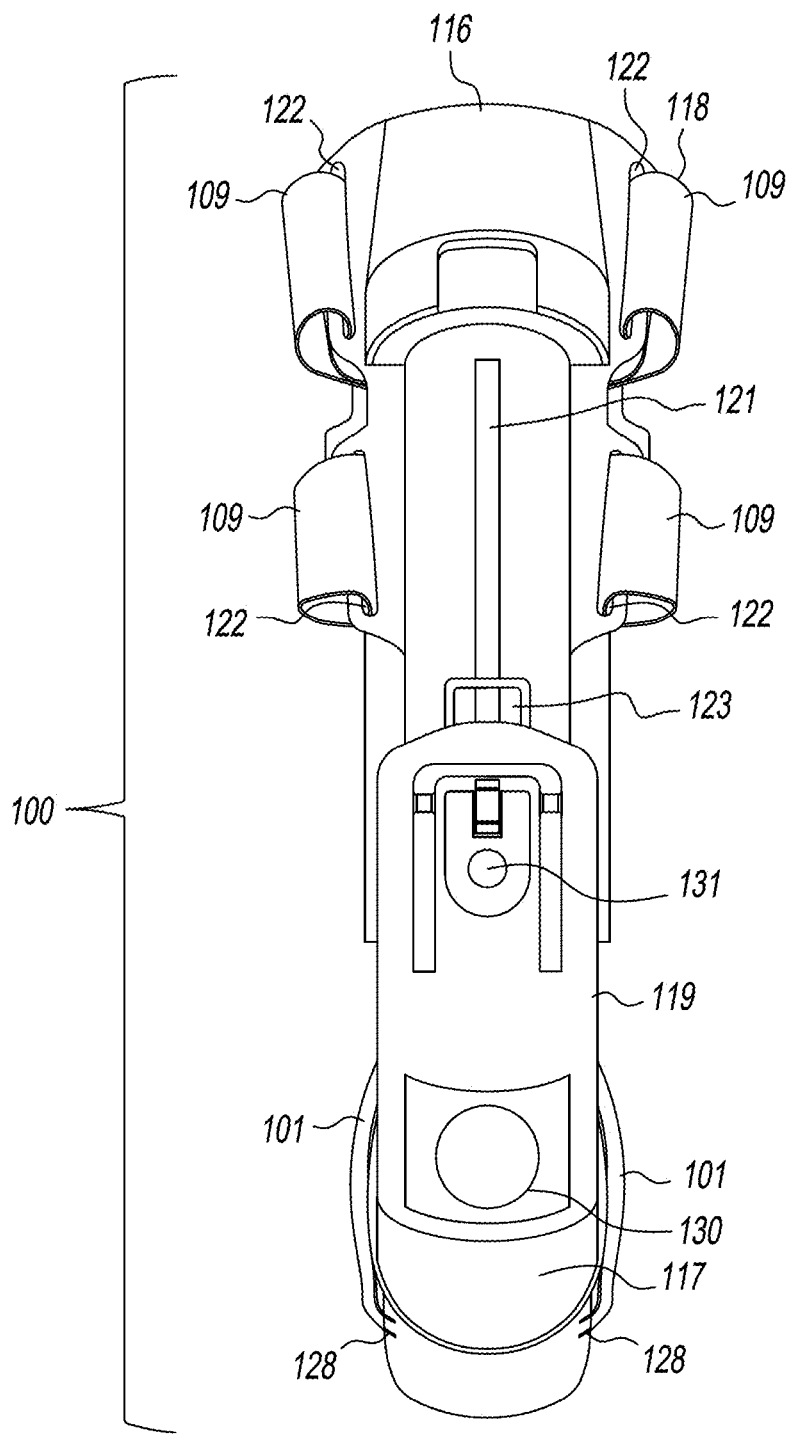
FIG. 10 is a rear view of one embodiment of the fully extended brace of FIG. 8.

FIG. 10 illustrates a rear view of a fully extended brace 100, including leg straps 109, and ankle strap 101. Ankle strap 101 is secured to brace 100 via heel openings 128. Slide 121 runs along the vertical center of the rear of slider 116. Slider 116 includes openings 122 to secure leg straps 109.

The top of receiver 119 includes opening 123.

Clip 131 pass through openings in both receiver 119 and slider 116. Clip 131 is engaged to keep slider 116 in a locked position. Clip 131 is loosened before slider 116 can change position, then slider 116 translates vertically. When brace 100 is fully extended, clip 131 passes through the bottom of slide 121 on slider 116. When brace 100 is fully contracted, clip 131 passes through the top of slide 121 on slider 116.

Figure 11:
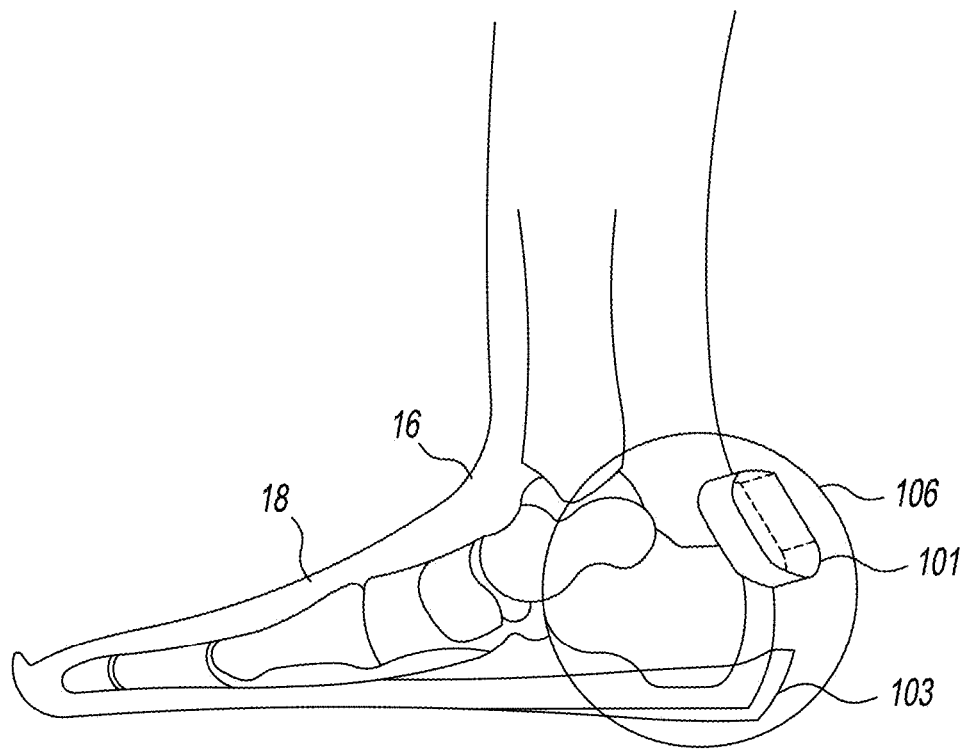
FIG. 11 is a side view of the heel and ankle contact points of the brace.

FIG. 11 illustrates the heel and ankle contact points in a side view of brace 100. Heel area 106 is circled, ankle strap 101 is molded to gently approach heel 36 and Achilles tendon 28. Footplate 103 does not require any additional tarsal straps.

Figure 12:
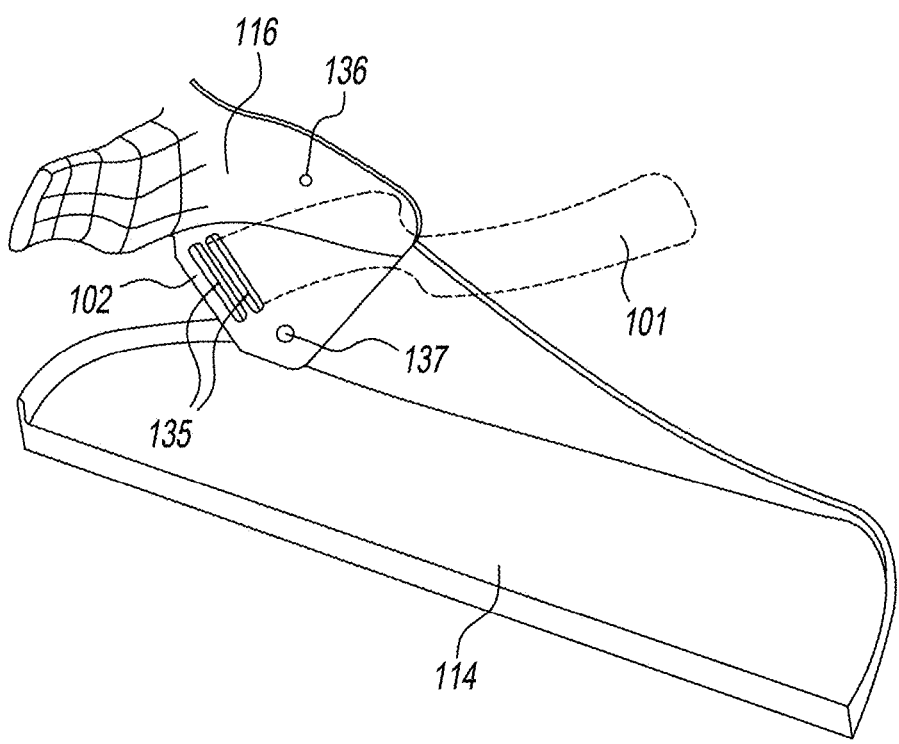
FIG. 12 is cross-sectioned perspective view of another embodiment of the brace wherein the ankle strap is secured to the receiver.

FIG. 12 illustrates a cross-section perspective view of the inside of another embodiment of brace 100 wherein receiver 119 and strap 101 are molded around Achilles tendon 28. Strap 101 attaches to the inside of receiver 119 via openings 135. Openings 135 are at a 45 degree angle relative to a horizontal plane.

The flexion angle of brace 100 is affixed via bolts 136. Additional means 136 for affixing the flexion angle are also envisioned.

Both bolts 136 and bolts 137 secure receiver 119 to boot 114. Additional means 137 for securing receiver 119 to the boot 114 are also envisioned.

Figure 13:
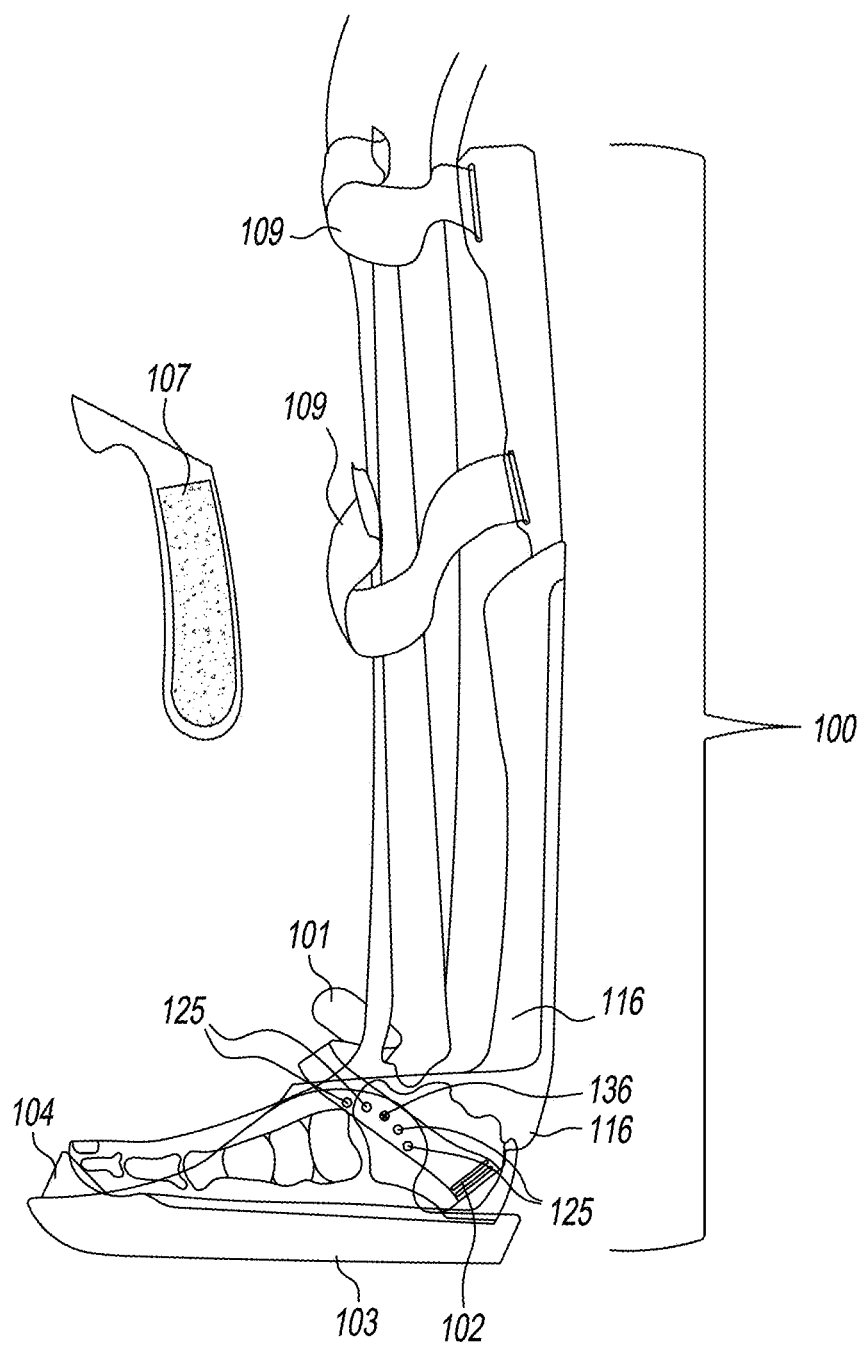
FIG. 13 is a stylized perspective view of an embodiment of the brace wherein the ankle strap is secured to the receiver.

Another embodiment of a fully extended brace 100 is illustrated in FIG. 13. Brace 100 includes an ankle strap 101 secured via openings 102 in receiver 119. Brace 100 may also include toe wedge 104. Molded boot 103 does not require any additional midfoot straps.

Receiver 119 is secured to molded boot 103 via bolts 136. The flexion angle of molded boot 103 is varied by changing openings 125.

Leg straps 109 and ankle strap 101 may terminate with fasteners and hook and loop 107.

Figure 14:
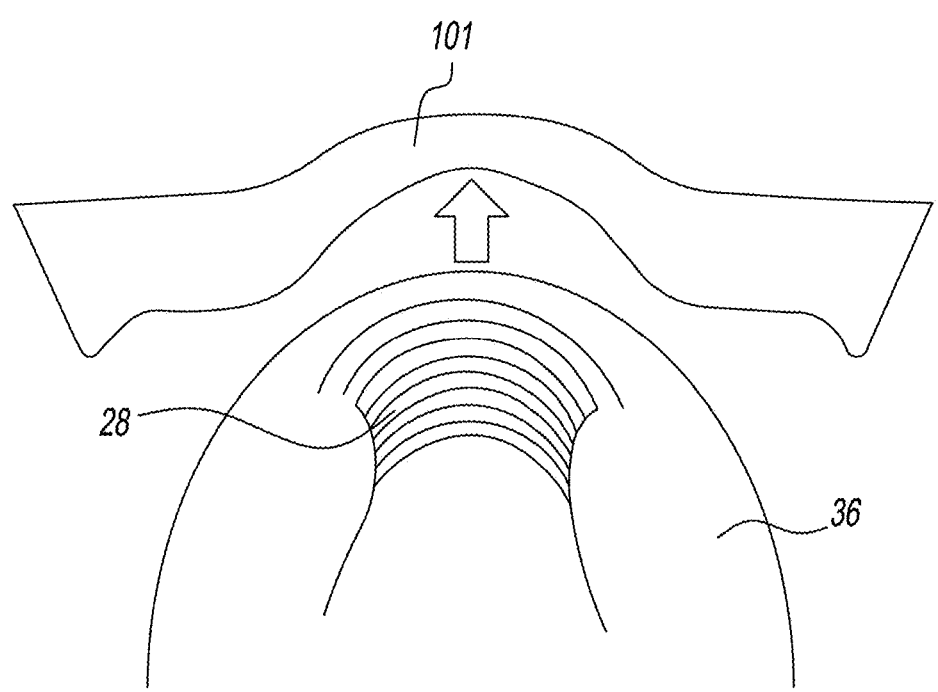
FIG. 14 is a top view of the curvature in the mold of ankle strap of the brace.

FIG. 14 illustrates the curvature in strap 101 to reduce pain and friction to the heel. Strap 101 is molded around Achilles tendon 28 and heel 36.

Figure 15:
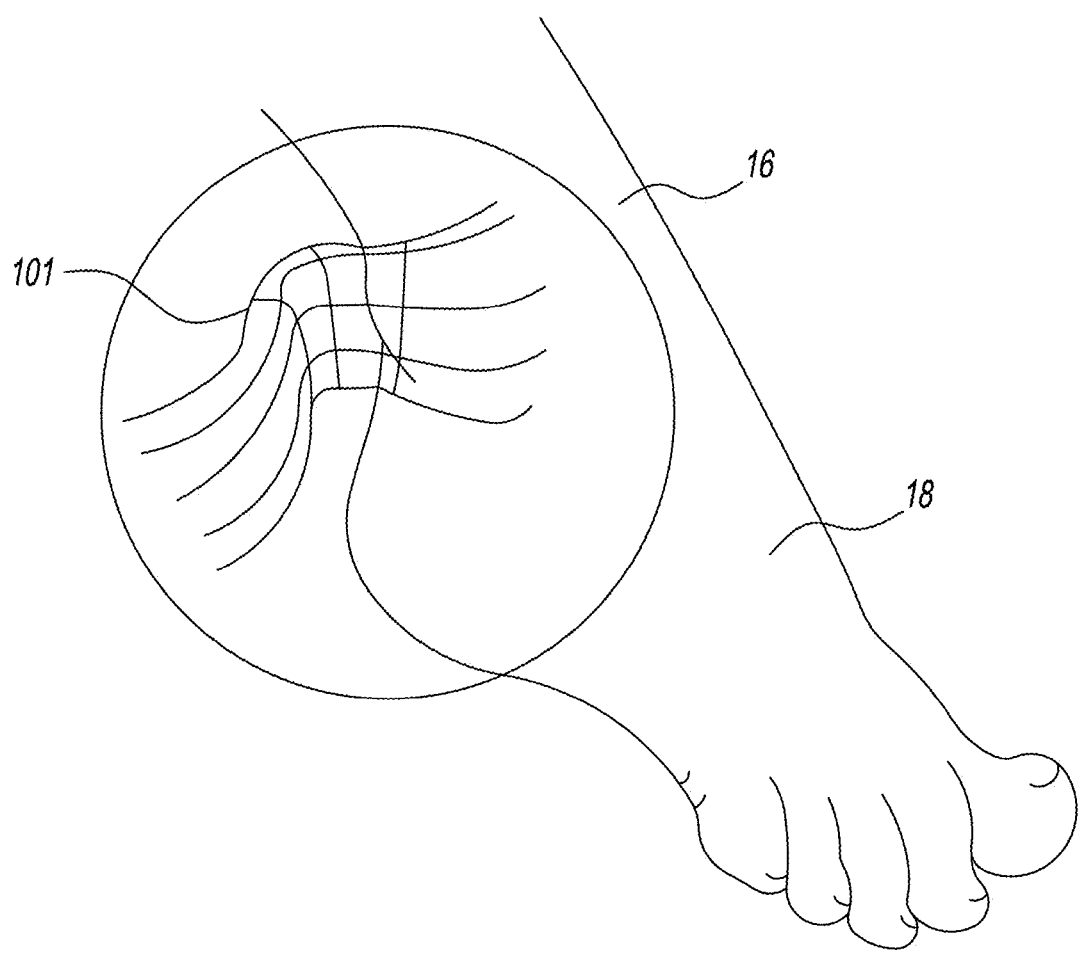
FIG. 15 is perspective view of a foot and the placement of the molded ankle strap.

FIG. 15 illustrates the configuration of the mold of ankle strap 101 around Achilles tendon 28 and heel 36.

Figure 16:
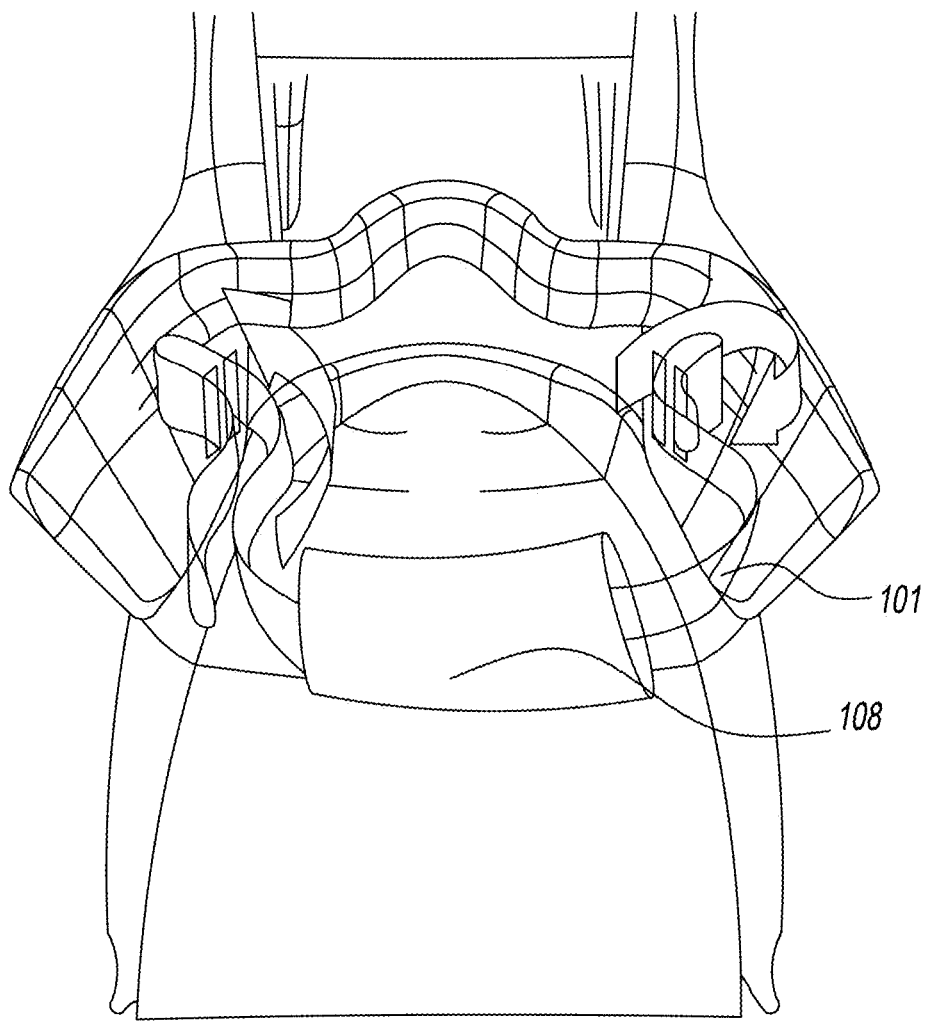
FIG. 16 is a normal view of the brace, before placing the foot inside, showing the order numerically to feed and fasten the strap.

FIG. 16 illustrates the strap configuration. The steps to secure ankle strap 101 are as follows: First feed the strap 101 through the farthest back openings and fasten with a D-loop to anchor. Then feed the strap 101 back through the farthest opening to the outside. Finally feed the strap 101 back inside the brace through the openings and fasten to the top. Padding 109 may be included on strap 101.

Figure 17:
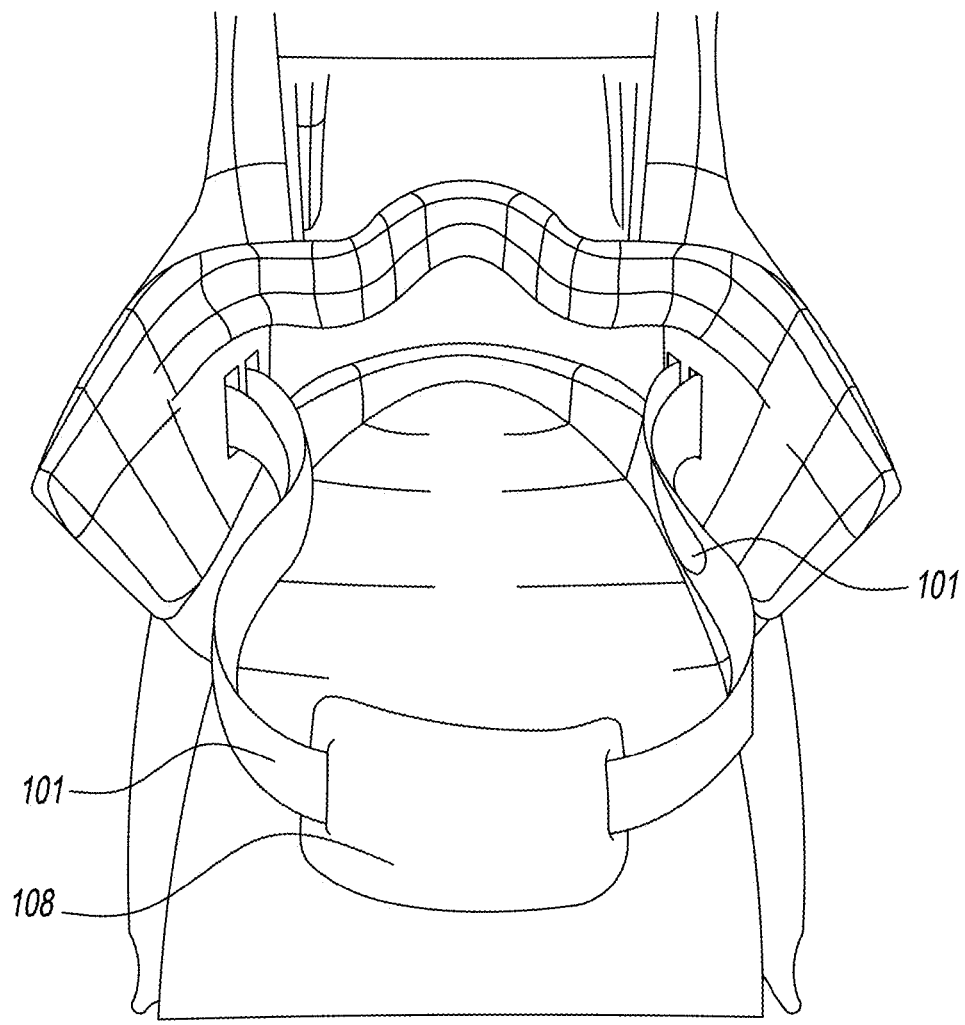
FIG. 17 is a normal view of the brace, before placing the foot inside, showing the fastened strap.

FIG. 17 illustrates the normal view of ankle strap 101 before placing a foot inside the boot. Padding 109 may be included on strap 101.

Figure 18:
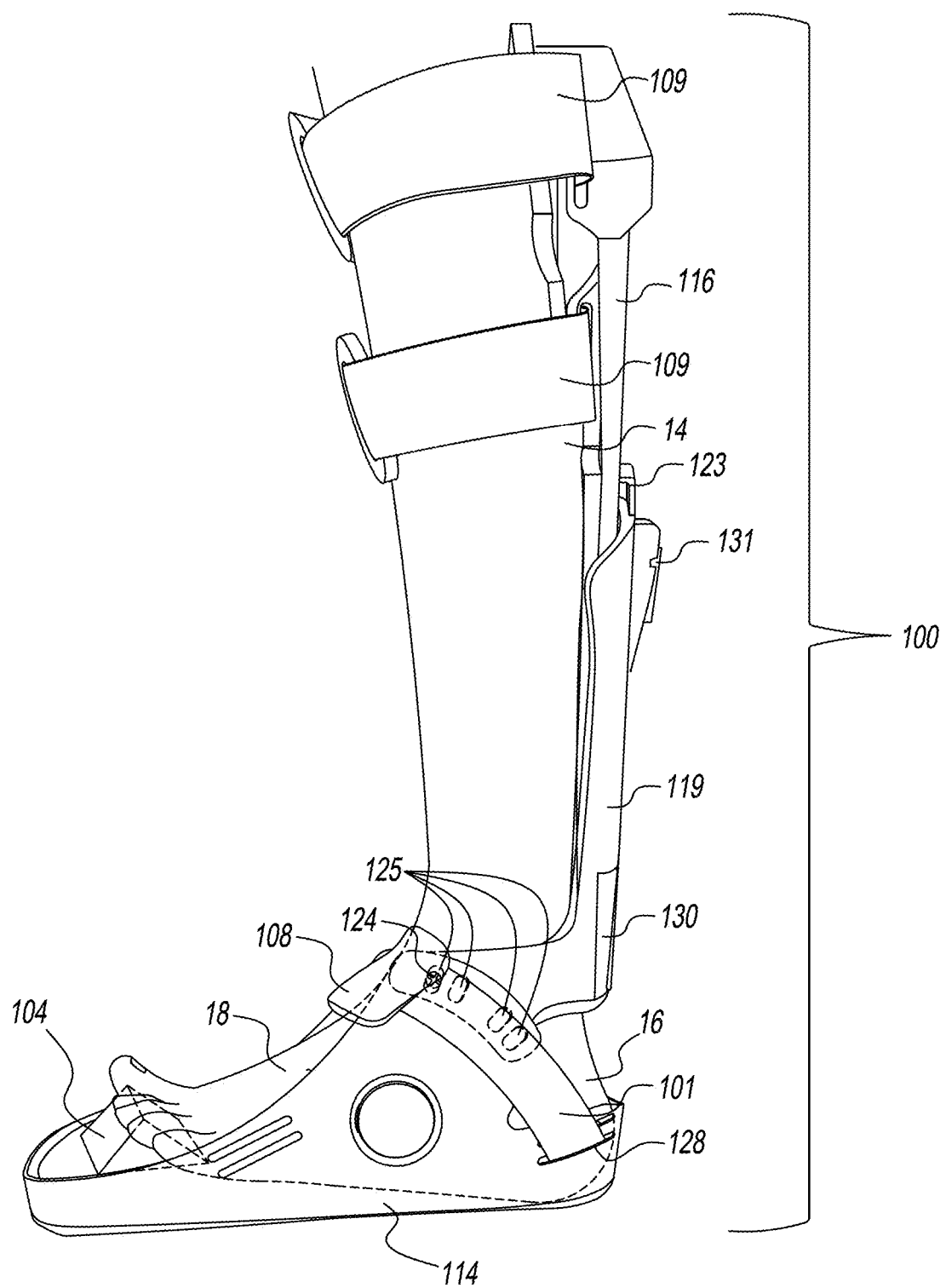
FIG. 18 is a side view of a foot and ankle in dorsiflexion in the brace.

FIG. 18 is a side view of a foot 18 in brace 100, while ankle 16 is dorsiflexing. Bolt 124 is in the left most opening 125 of boot 114. Ankle strap 101 with pad 108 is secured to boot 114 via heel openings 128.

Figure 19:
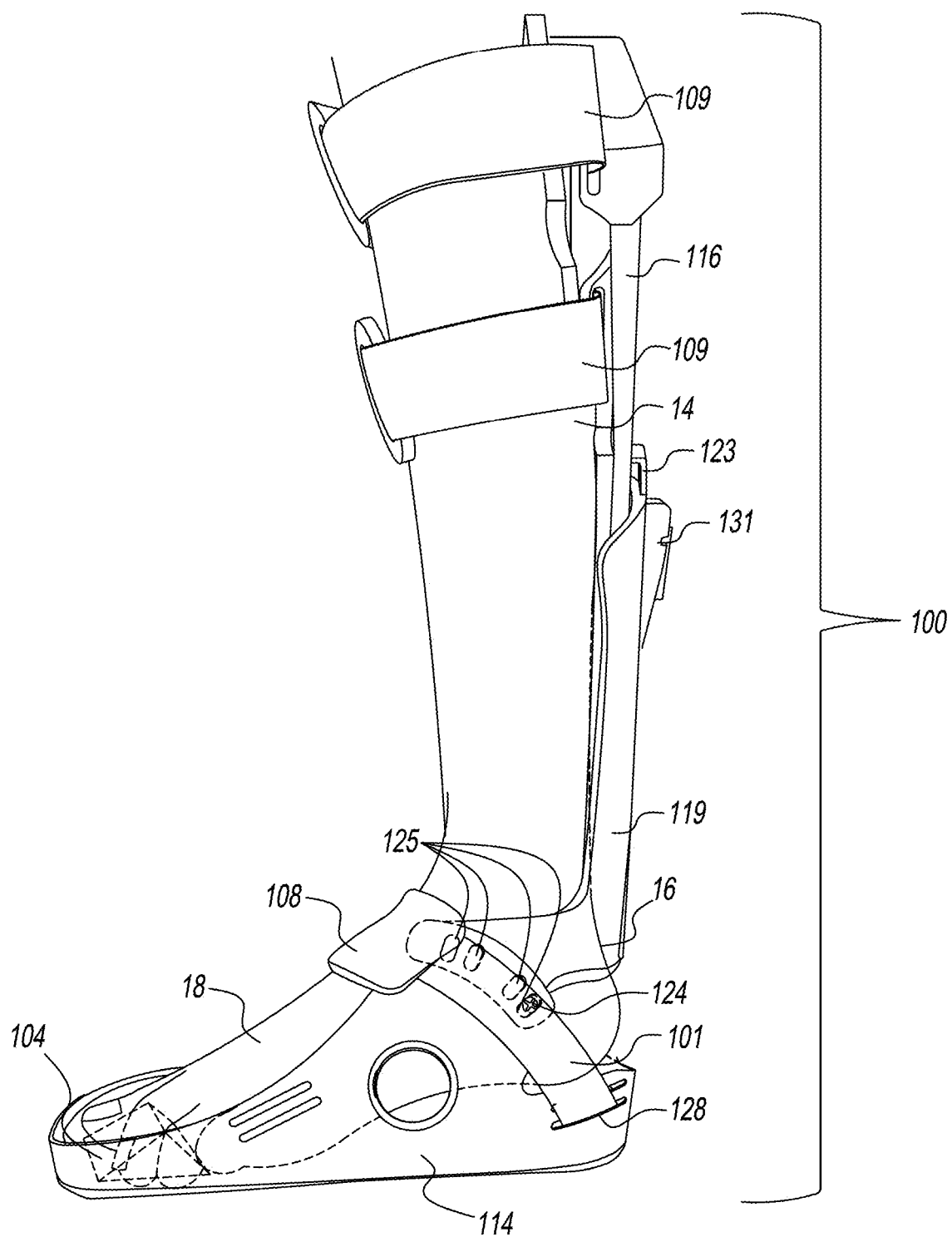
FIG. 19 is a side view of a foot and ankle in plantar flexion in the brace.

FIG. 19 is a side view of foot 18 in fully extended brace 100, while ankle 16 is plantar flexing and the knee is fully extended. Bolt 124 is in the right most opening 125 of boot 114. Ankle strap 101 with pad 108 is secured to boot 114 via heel openings 128.

FIG. 19 illustrates a method of treating foot and ankle conditions by stretching the Gastrocnemius, Soleus, and Plantaris muscles, the method comprising the steps of: simultaneously extending the knee of the user and plantar-flexing the ankle by using brace 100.

Figure 20:
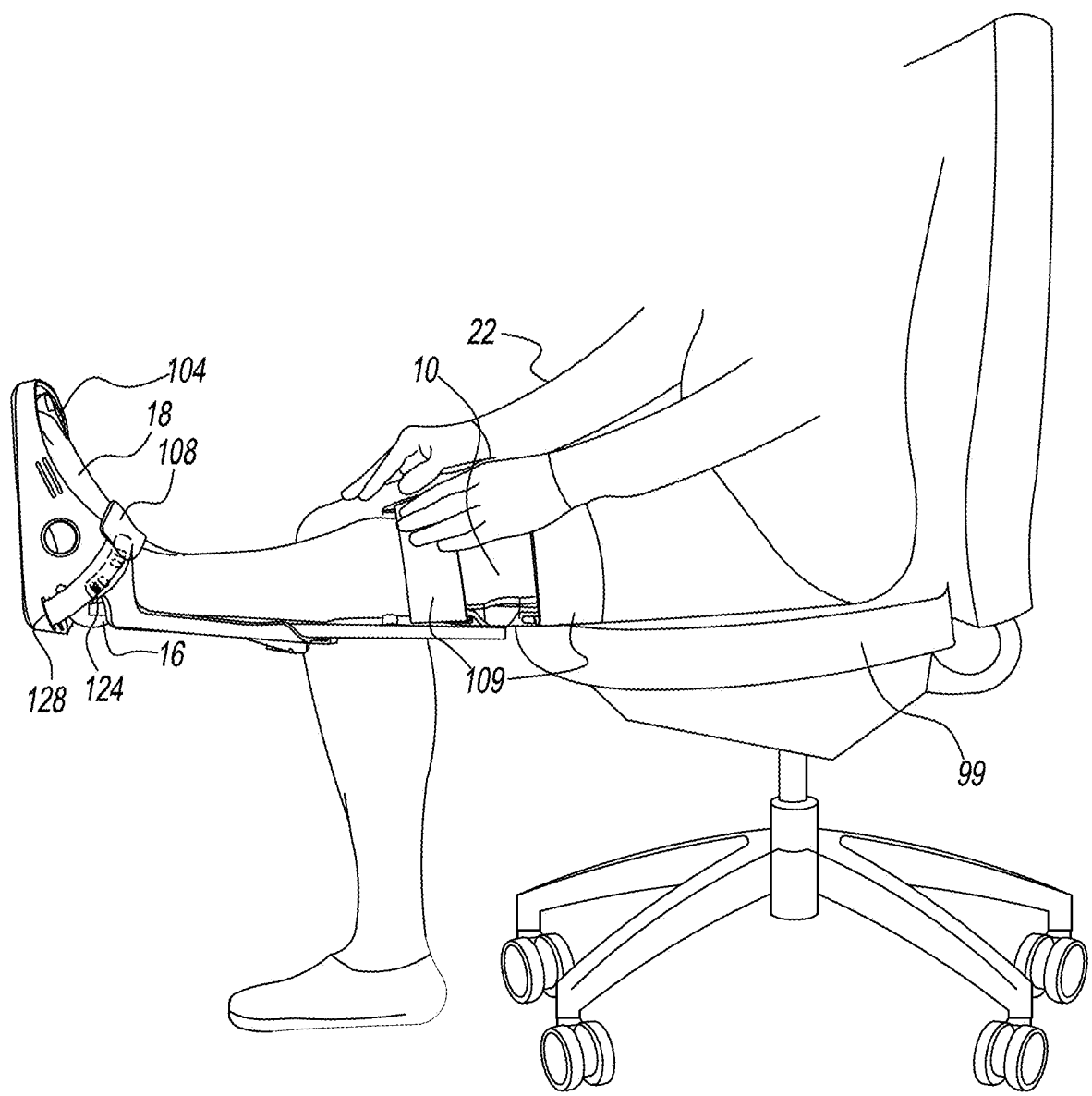
FIG. 20 is a side view of a user in the brace sitting in a chair, with a non-extended knee and plantar flexing the ankle.

FIG. 20 is a side view of user 22 in a non-extended brace 100 sitting in chair 99. Ankle 16 is in plantar flexion. Ankle strap 101 with pad 108 is secured to boot 114 via heel openings 128. Leg straps 109 are secured around the lower leg and calf 14.

Figure 21:
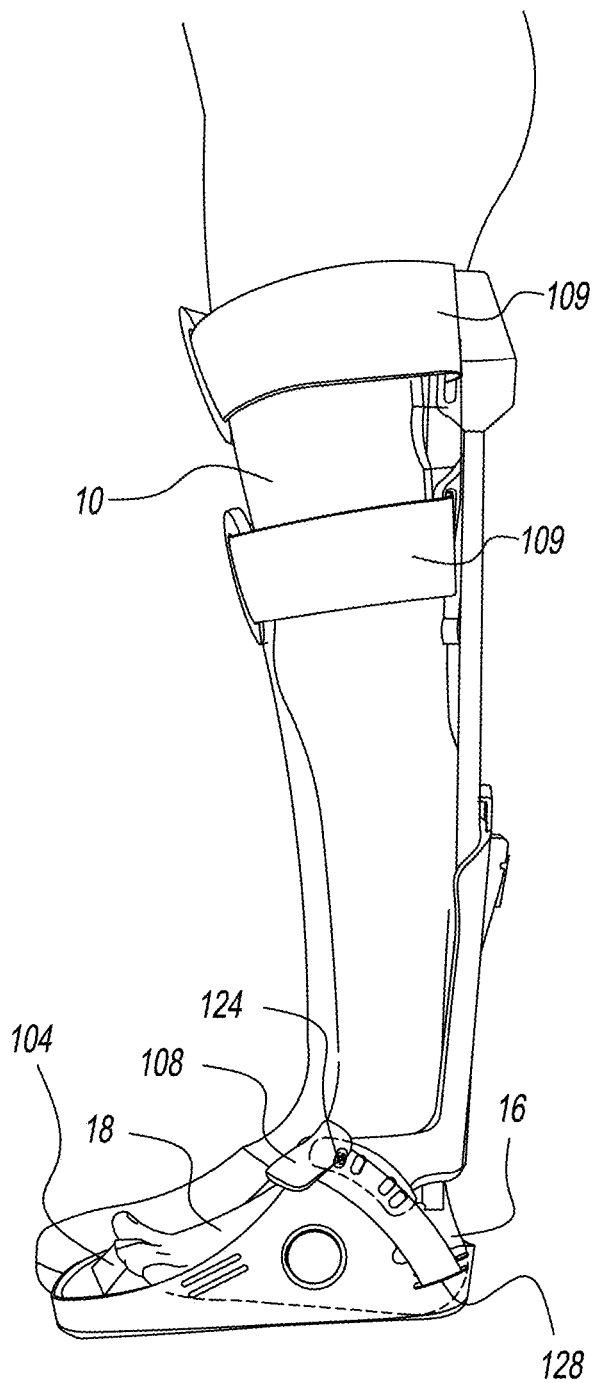
FIG. 21 is a side view of user in the brace standing with a fully extended knee and the ankle in dorsiflexion.

FIG. 21 is a side view of user 22 standing in a fully extended brace 100. Ankle 16 is in dorsiflexion. Ankle strap 101 with pad 108 is secured to boot 114 via heel openings 128. Leg straps 109 are secured around thigh 10.

FIG. 21 illustrates a method of treating foot and ankle conditions by stretching the Gastrocnemius, Soleus, and Plantaris muscles, the method comprising the steps of: extending the knee of the user and the ankle of the user in dorsiflexion by using brace 100. The method of treating foot and ankle conditions is associated with any condition selected from the group consisting of: Heel Spur Syndrome, Plantar fasciitis, equinus related to neuromuscular disorders including disorders selected from the group consisting of Cerebral Palsy and Friedreich's Ataxia, Congenital disorders including disorders selected from the group consisting of Congenital equinus, Clubfoot. Vertical Talus and Calcaneal Valgus, Pediatric Flexible Flatfoot deformity, Adult Flexible Flatfoot deformity, muscle strains, stress fractures, shin splints or Medial tibial stress syndrome, Iliotibial band syndrome, patellofemoral syndrome, ankle sprains or fractures, metatarsal or forefoot pain, metatarsophalangeal joint (MPJ) synovitis, hallux abducto valgus, hammer toes or claw toes, Lis franc's or Midfoot arthrosis, hallux limitus or hallux rigidus, forefoot calluses, Morton's neuroma, Chronic ankle instability, Sever's disease, lateral foot pain, Genu recurvatum, lower back pain, arch pain, ankle arthrosis, subtalar arthrosis, sesamoiditis, anterior compartment syndrome, forefoot nerve entrapment, Tibialis Posterior Tendon Dysfunction, Achilles tendonitis and tendonosis, Achilles tendon injuries, Haglund's Deformity, Retrocalcaneal heel spurs and tendonosis, equinus related to tarsal coalitions, Bunion deformities, Metatarsalgia, Forefoot pain, Charcot deformity, Diabetic forefoot ulcers and toe ulcers, Equinovarus deformities from post-injury or post-stroke patients, Post Transmetatarsal or Chopart's amputation patients, Midfoot degenerative joint disease at Lis Franc's joint or Chopart's joint, Hypermobile first ray disorders and Cross-over toe deformities, equinus related to myelomeningocele, Flexor Hallucis Longus Tendinosis, Anterior Ankle Impingement.

While the inventions have been illustrated and described in detail in the drawings and foregoing description, the same is to be considered as illustrative and not restrictive in character, it being understood that the preferred embodiment has been shown and described and that changes and modifications that come within the spirit of the invention are desired to be protected.

What is claimed is:

1. A brace for treating foot and ankle conditions by stretching a gastrocnemius muscle, a soleus muscle, and a plantaris muscle, the brace comprising:
   a receiver, an adjustable slider, a boot, wherein the receiver is configured to attach to the boot, wherein the boot includes openings for fixing an angle of dorsiflexion for an ankle of a user; wherein the boot includes a bottom plate,
   wherein an ankle hinge of the receiver and the boot create an heel opening for a heel of a user;
   the adjustable slider configured to be attached adjacent to the receiver above the heel, the adjustable slider defining a center slot extending along a substantial length of the adjustable slider, wherein the adjustable slider extends vertically to change an overall length of the brace to accommodate different leg lengths of different users;
   a clip configured for connecting the adjustable slider and the receiver; and
   a wedge supported by the boot, wherein the brace locks a knee in extension while also locking an ankle of a user in a dorsiflexion position at times or a normal position at other times;
   wherein the brace permits a 40 degree change in flexion angle allowing for 20 degrees of dorsiflexion and 20 degrees of plantarflexion.

2. The brace of claim 1, further comprising a support bridging two interior faces of the receiver.

3. The brace of claim 1, wherein the flexion angle is controlled by inserting a fastener to secure into one of several first openings of an ankle joint axis on one side of the boot, and also inserting the fastener to secure into a second opening in a same side of the receiver.

4. The brace of claim 3 where the fastener is a screw.

5. The brace of claim 1, further comprising a toe wedge.

6. The brace of claim 1, further comprising an ankle strap secured to a side of the brace at a 45 degree angle.

7. The brace of claim 1, wherein the brace is molded to a curvature of a heel and an Achilles tendon to reduce pain and friction to the heel.

8. The brace of claim 1, wherein an ankle strap is secured to the receiver.

9. The brace of claim 1, wherein an ankle strap is secured to the boot.

10. A method of treating foot and ankle conditions by stretching a Gastrocnemius, a soleus, and a plantaris muscle, the method comprising the steps of:

extending a knee of a user while the foot and ankle of the user is dorsiflexed by using the brace of claim 1.

11. The method of claim 10, wherein the foot and ankle conditions is associated with any condition selected from the group consisting of:
  a. Heel Spur Syndrome, Plantar fasciitis
  b. equinus related to Neuromuscular disorders including disorders selected from the group consisting of Cerebral Palsy and Friedreich's Ataxia
  c. Congenital disorders including disorders selected from the group consisting of Congenital equinus, Clubfoot, Vertical Talus and Calcaneal Valgus
  d. Pediatric Flexible Flatfoot deformity
  e. Adult Flexible Flatfoot deformity
  f. Tibialis Posterior Tendon Dysfunction
  g. Achilles tendonitis
  h. Achilles tendon injuries
  i. Haglund's Deformity
  j. Retrocalcaneal heel spurs and tendonosis
  k. equinus related to Tarsal Coalitions
  l. Bunion deformities
  m. Metatarsalgia
  n. Forefoot pain
  o. Charcot deformity
  p. Diabetic forefoot ulcers and toe ulcers
  q. Equinovarus deformities from post-injury or post-stroke patients
  r. Post Transmetatarsal or Chopart's amputation patients
  s. Midfoot degenerative joint disease at Lis Franc's joint or Chopart's joint
  t. Hypermobile first ray disorders and
  u. Cross-over toedeformities.

12. The method of claim 10, wherein the foot and ankle conditions are associated with any condition selected from the group consisting of:
  a. muscle strains,
  b. stress fractures,
  c. shin splints or Medial tibial stress syndrome,
  d. Iliotibial band syndrome,
  e. patellofemoral syndrome,
  f. ankle sprains or fractures,
  g. metatarsal pain,
  h. metatarsophalangeal joint (MPJ) synovitis,
  i. hallux abducto valgus,
  j. hammer toes or claw toes,
  k. Lis franc's or Midfoot arthrosis,
  l. hallux limitus or hallux rigidus,
  m. forefoot calluses,
  n. Morton's neuroma,
  o. Chronic ankle instability,
  p. Sever's disease,
  q. lateral foot pain,
  r. Genu recurvatum,
  s. lower back pain,
  t. arch pain,
  u. ankle arthrosis,
  v. subtalar arthrosis,
  w. sesamoiditis,
  x. anterior compartment syndrome,
  y. forefoot nerve entrapment,
  z. Tibialis Posterior Tendon Dysfunction
  aa. Achilles tendonitis and tendonosis
  bb. Achilles tendon injuries
  cc. equinus related to myelomeningocele
  dd. Flexor Hallucis Longus Tendinosis and
  ee. Anterior Ankle Impingement.

* * * * *